(12) United States Patent
Addison et al.

(10) Patent No.: US 10,610,164 B2
(45) Date of Patent: Apr. 7, 2020

(54) DETERMINING CHANGES TO AUTOREGULATION

(71) Applicant: Covidien LP, Mansfield, MA (US)

(72) Inventors: Paul S. Addison, Edinburgh (GB); Dean Montgomery, Edinburgh (GB); Andre Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 155 days.

(21) Appl. No.: 15/962,503

(22) Filed: Apr. 25, 2018

(65) Prior Publication Data

US 2019/0328337 A1 Oct. 31, 2019

(51) Int. Cl.
*A61B 5/02* (2006.01)
*A61B 5/00* (2006.01)
(Continued)

(52) U.S. Cl.
CPC ............ *A61B 5/7275* (2013.01); *A61B 5/021* (2013.01); *A61B 5/026* (2013.01);
(Continued)

(58) Field of Classification Search
CPC ..... A61B 5/02028; A61B 5/021; A61B 5/026; A61B 5/0261; A61B 5/4058; A61B 5/4064; A61B 5/7275; A61B 5/7282; A61B 5/746
See application file for complete search history.

(56) References Cited

U.S. PATENT DOCUMENTS 4,688,577 A 8/1987 Bro
5,579,774 A 12/1996 Miller et al.
(Continued)

FOREIGN PATENT DOCUMENTS

CN 100399990 A 12/2006
DE 10331027 A1 1/2005
(Continued)

OTHER PUBLICATIONS

Ameloot et al., "An observational near-infrared spectroscopy study on cerebral autoregulation in post-cardiac arrest patients: Time to drop 'one-size-fits-all' hemodynamic targets?," Resuscitation 90, Jan. 121-126, 2015.
(Continued)

*Primary Examiner* — Eugene T Wu
(74) *Attorney, Agent, or Firm* — Shumaker & Sieffert, P.A.

(57) ABSTRACT

In some examples, a device includes a memory configured to store a first relationship between a blood pressure and another physiological parameter of a patient, the first relationship being indicative of cerebral autoregulation of the patient. The device also includes processing circuitry configured to receive first and second signals indicative of the blood pressure and the physiological parameter, respectively, of a patient. The processing circuitry is also configured to determine an expected value and an actual value of the physiological parameter at a particular blood pressure value of the first physiological signal. The processing circuitry is configured to determine, based on a difference between the actual value and the expected value, and store, in the memory, a second relationship between the blood pressure and the physiological parameter, the second relationship being indicative of a change in the cerebral autoregulation of the patient from the first relationship.

20 Claims, 6 Drawing Sheets

(51) Int. Cl.
*A61B 5/021* (2006.01)
*A61B 5/03* (2006.01)
*A61B 5/026* (2006.01)

(52) U.S. Cl.
CPC ............ *A61B 5/02028* (2013.01); *A61B 5/03* (2013.01); *A61B 5/7246* (2013.01)

(56) References Cited

U.S. PATENT DOCUMENTS

| | | | |
|---|---|---|---|
| 6,438,399 | B1 | 8/2002 | Kurth |
| 6,599,251 | B2 | 7/2003 | Chen et al. |
| 6,875,176 | B2 | 4/2005 | Mourad et al. |
| 7,532,919 | B2 | 5/2009 | Soyemi et al. |
| 7,744,541 | B2 | 6/2010 | Baruch et al. |
| 7,998,075 | B2 | 8/2011 | Ragauskas et al. |
| 8,057,398 | B2 | 11/2011 | McNames et al. |
| 8,062,224 | B2 | 11/2011 | Ragauskas et al. |
| 8,211,022 | B2 | 7/2012 | Lo et al. |
| 8,366,627 | B2 | 2/2013 | Kashif et al. |
| 8,433,384 | B2 | 4/2013 | Bechtel et al. |
| 8,512,260 | B2 | 8/2013 | Grudic et al. |
| 8,556,811 | B2 | 10/2013 | Brady |
| 8,852,094 | B2 | 10/2014 | Al-ali et al. |
| 9,192,330 | B2 | 11/2015 | Lin et al. |
| 9,861,317 | B2 | 1/2018 | Ochs |
| 2002/0099295 | A1 | 7/2002 | Gil et al. |
| 2003/0219797 | A1 | 11/2003 | Zhao et al. |
| 2009/0326386 | A1 | 12/2009 | Sethi et al. |
| 2010/0030054 | A1 | 2/2010 | Baruch et al. |
| 2011/0105912 | A1 | 5/2011 | Widman et al. |
| 2012/0004517 | A1 | 1/2012 | Starr et al. |
| 2012/0130697 | A1* | 5/2012 | Woodford ............ A61B 5/0205 703/11 |
| 2012/0253211 | A1 | 10/2012 | Brady et al. |
| 2013/0144140 | A1 | 6/2013 | Frederick et al. |
| 2013/0190632 | A1 | 7/2013 | Baruch et al. |
| 2014/0073888 | A1 | 3/2014 | Kim |
| 2014/0278285 | A1 | 9/2014 | Marmarelis et al. |
| 2015/0230758 | A1 | 8/2015 | Ochs |
| 2016/0081563 | A1 | 3/2016 | Wiard et al. |
| 2016/0106372 | A1 | 4/2016 | Addison et al. |
| 2016/0162786 | A1 | 6/2016 | Grudic et al. |
| 2016/0220115 | A1 | 8/2016 | Fisher et al. |
| 2016/0324425 | A1 | 11/2016 | Addison et al. |
| 2016/0367197 | A1 | 12/2016 | Addison et al. |
| 2017/0105631 | A1 | 4/2017 | Addison et al. |
| 2018/0014791 | A1 | 1/2018 | Montgomery et al. |
| 2018/0338731 | A1* | 11/2018 | Addison ................ G16H 50/20 |

FOREIGN PATENT DOCUMENTS

| | | |
|---|---|---|
| RU | 2465829 C1 | 11/2012 |
| WO | WO 2016015057 A1 | 1/2016 |

OTHER PUBLICATIONS

Brady, MD, et al., "Monitoring Cerebrovascular Autoregulation Refining care goals in the ICU," Apr. 21, 2009, 15 pp.
Brady, MD et al., "Real-time continuous monitoring of cerebral blood flow autoregulation using near-infrared spectroscopy in patients undergoing cardiopulmonary bypass," Stroke 41, pp. 1951-1956, Feb. 2010.
Brady, MD et al., "A Dynamic Association Between Cavopulmonary Shunt Pressure and Cerebrovascular Autoregulation in an Infant With Congenital Heart Disease and Intracranial Hemorrhage," J. Cardiothorac. Vasc. Anesth. Vo. 23, No. 2, pp. 215-218; Apr. 2009.
Brady, MD et al., "Continuous Measurement of Autoregulation by Spontaneous Fluctuations in Cerebral Perfusion Pressure: Comparison of 3 Methods," Stroke. 39, pp. 2531-2537; Sep. 2008.
Brady, MD et al., "Continuous Monitoring of Cerebrovascular Pressure Reactivity After Traumatic Brain Injury in Children," Pediatrics 124, e1205-e1212, Dec. 2009.
Brady, MD et al., "Continuous Time-Domain Analysis of Cerebrovascular Autoregulation Using Near-infrared Spectroscopy," Stroke 38, pp. 2818-2825; Oct. 2007.
Brady, MD et al., "Monitoring Cerebral Blood Flow Pressure Autoregulation in Pediatric Patients During Cardiac Surgery," Stroke 41, 1957-1962, Sep. 2010.
Brady, MD et al., "Noninvasive Autoregulation Monitoring With and Without Intracranial Pressure in the Naïve Piglet Brain," Anesth. Analg. vol. 111, No. 1, 191-195; Jul. 2010.
Budohoski, MD et al., "Bilateral Failure of Cerebral Autoregulation is Related to Unfavorable Outcome After Subarachnoid Hemorrhage," Neurocrit. Care 22, 65-73, Jul. 2014.
Budohoski, MD, et al., "The Relationship Between Cerebral Blood Flow Autoregulation and Cerebrovascular Pressure Reactivity After Traumatic Brain Injury," Neurosurgery 71, pp. 652-660 May 2012.
Calviere et al., "Prediction of Delayed Cerebral Ischemia After Subarachnoid Hemorrhage Using Cerebral Blood Flow Velocities and Cerebral Autoregulation Assessment," Neurocrit. Care, Feb. 2015.
Czosnyka, PhD, et al., "Intracranial pressure: More Than a Number," Neurosurg. Focus 22, E10, May 2007.
Czosnyka, PhD, et al., "Monitoring of Cerebrovascular Autoregulation: Facts, myths, and missing links," Neurocrit. Care 10, 373-386, Jan. 2009.
Czosnyka, PhD, et al., "Monitoring of Cerebral Autoregulation in Head-Injured Patients," Stroke. 27, 1829-1834, Oct. 1996.
Depreitere et al., "Pressure autoregulation monitoring and cerebral perfusion pressure target recommendation in patients with severe traumatic brain injury based on minute-by-minute monitoring data," J. Neurosurg. 120, pp. 1451-1457, Apr. 2014.
Dias et al., "Kidney-Brain Link in Traumatic Brain Injury Patients? A preliminary report," Neurocrit. Care, Oct. 2014, 12 pp.
Dias et al., "Optimal Cerebral Perfusion Pressure Management at Bedside: A Single-Center Pilot Study," Neurocrit. Care, Jan. 2015, 13 pp.
Diedler, MD et al., "The Limitations of Near-Infrared Spectroscopy to Assess CerebrovascularR: The Role of Slow Frequency Oscillations," Anesth. Analg. vol. 113 No. 4, pp. 849-857, Oct. 2011.
Donnelly et al., "Further understanding of cerebral autoregulation at the bedside: possible implications for future therapy," Expert Rev. Neurother. 15, pp. 169-185, Jan. 2015.
Eide, MD, PhD., et al. "Pressure-derived versus pressure wave amplitude—derived indices of cerebrovascular pressure reactivity in relation to early clinical state and 12-month outcome following aneurysmal subarachnoid hemorrhage," J. Neurosurg. 116, pp. 961-971, May 2012.
Gilmore et al., "Relationship between cerebrovascular dysautoregulation and arterial blood pressure in the premature infant," J. Perinatol. 31, pp. 722-729, Mar. 2011.
Hori et al., "Effect of carotid revascularization on cerebral autoregulation in combined cardiac surgery," Eur. J. Cardio-Thoracic Surg., Feb. 2015, 7 pp.
Howells et al., "An optimal frequency range for assessing the pressure reactivity index in patients with traumatic brain injury," J. Clin. Monit. Comput., pp. 97-105, Mar. 2014.
Howlett et al., "Cerebrovascular autoregulation and neurologic injury in neonatal hypoxic-ischemic encephalopathy," Pediatr. Res. vol. 74, No. 5, pp. 525-535, Nov. 2013.
Jaeger, MD et al., "Effects of cerebrovascular pressure reactivity-guided optimization of cerebral perfusion pressure on brain tissue oxygenation after traumatic brain injury," Crit. Care Med. vol. 38, No. 5, pp. 1343-1347, May 2010.
Jaeger, MD, et al., "Continuous monitoring of cerebrovascular autoregulation after subarachnoid hemorrhage by brain tissue oxygen pressure reactivity and its relation to delayed cerebral infarction," Stroke 38, pp. 981-986, Apr.-May 2007.
Kvandal et al., "Impaired cerebrovascular reactivity after acute traumatic brain injury can be detected by wavelet phase coherence analysis of the intracranial and arterial blood pressure signals," J. Clin. Monit. Comput. 27, pp. 375-383, May 2013.
Laflam et al., "Shoulder Surgery in the Beach Chair Position Is Associated with Diminished Cerebral Autoregulation but No Differences in Postoperative Cognition or Brain Injury Biomarker

(56) References Cited

OTHER PUBLICATIONS

Levels Compared with Supine Positioning," Anesth. Analg. vol. 120, No. 1, pp. 176-185, Jan. 2015.
Lang MD, PhD, et al., "A Review of Cerebral Autoregulation: Assessment and Measurements," Aust. Anaesth. 161-172, 2005, (Applicant points out, in accordance with MPEP 609.04(a), that the year of publication, 2005, is sufficiently earlier than the effective U.S. filing date, Mar. 5, 2018, so that the particular month of publication is not in issue.).
Lang et al., "Short pressure reactivity index versus long pressure reactivity index in the management of traumatic brain injury," J. Neurosurg. vol. 122, pp. 588-594, Mar. 2015.
Lang et al., "Continuous monitoring of cerebrovascular autoregulation: a validation study," J. Neurol. Neurosurg. Psychiatry 72, pp. 583-586, Jan. 2002.
Lee et al., "A pilot study of cerebrovascular reactivity autoregulation after pediatric cardiac arrest," Resuscitation 85, pp. 1387-1393, Jun. 2014.
Lee, J. K. et al., "Cerebral blood flow and cerebrovascular autoregulation in a swine model of pediatric cardiac arrest and hypothermia*," Crit. Care Med. vol. 39, No. 10, pp. 2337-2345, Oct. 2011.
Lee, MD et al., "Cerebrovascular Reactivity Measured by Near-Infrared Spectroscopy," Stroke 40, pp. 1820-1826, Oct. 2009.
Lee, MD, et al., "Noninvasive autoregulation monitoring in a swine model of pediatric cardiac arrest," Anesth. Analg. vol. 114, pp. 825-836, Apr. 2012.
Lewis et al., "Continuous Correlation Between Intracranial Pressure and Cerebral Blood Flow Velocity Reflects Cerebral Autoregulation Impairment During Intracranial Pressure Plateau Waves," Neurocrit. Care 21, pp. 514-525, May 2014.
Liu et al., "Comparison of frequency and time domain methods of assessment of cerebral autoregulation in traumatic brain injury," J. Cereb. Blood Flow Metab. 35, pp. 248-256, Nov. 2014.
Nasr et al., "Baroreflex and Cerebral Autoregulation Are Inversely Correlated," Circ. J. vol. 78, pp. 2460-2467, Oct. 2014.
Nasr et al., "Cerebral autoregulation in patients with obstructive sleep apnea syndrome during wakefulness," Eur. J. Neurol. 16, pp. 386-391, Mar. 2009.
Ono, MD et al., "Blood pressure excursions below the cerebral autoregulation threshold during cardiac surgery are associated with acute kidney injury," Crit. Care Med. 41, pp. 464-471, Feb. 2013.
Ono, MD et al., "Cerebral Blood Flow Autoregulation Is Preserved After Hypothermic Circulatory Arrest," Ann. Thorac. Surg. 96, pp. 2045-2053, Dec. 2013.
Ono, MD et al., "Duration and magnitude of blood pressure below cerebral autoregulation threshold during cardiopulmonary bypass is associated with major morbidity and operative mortality," J. Thorac. Cardiovasc. Surg. 147, pp. 483-489, Jan. 2014.
Ono, MD et al., "Risks for impaired cerebral autoregulation during cardiopulmonary bypass and postoperative stroke," Br. J. Anaesth. 109, pp. 391-398, Jun. 2012.
Ono, MD et al., "Validation of a Stand-Alone Near-Infrared Spectroscopy System for Monitoring Cerebral Autoregulation During Cardiac Surgery," Anesth. Analg. vol. 116, No. 1, pp. 198-204, Jan. 2013.
Papademetriou et al., "Multichannel near infrared spectroscopy indicates regional variations in cerebral autoregulation in infants supported on extracorporeal membrane oxygenation," J. Biomed. Opt., vol. 17, pp. 067008-1-067008-9, Jun. 2012.
Radolovich et al., "Pulsatile Intracranial Pressure and Cerebral Autoregulation After Traumatic Brain Injury," Neurocrit. Care 15, pp. 379-386, Dec. 2011.
Radolovich et al., "Reactivity of Brain Tissue Oxygen to Change in Cerebral Perfusion Pressure in Head Injured Patients," Neurocrit. Care 10, pp. 274-279, Feb. 2009.
Reinhard, MD et al., "Cerebral Autoregulation in Carotid Artery Occlusive Disease Assessed From Spontaneous Blood Pressure Fluctuations by the Correlation Coefficient Index," Stroke 34, pp. 2138-2144, May 2003.

Reinhard, MD et al., "Cerebral dysautoregulation and the risk of ischemic events in occlusive carotid artery disease," J. Neurol. 255, pp. 1182-1189, Jun. 2008.
Schmidt et al., "Impaired autoregulation is associated with mortality in severe cerebral diseases" Clinical Neurosciences and Mental Health, 1 (Suppl. 1), May 2014, 6 pp.
Schmidt et al., "Asymmetry of cerebral autoregulation does not correspond to asymmetry of cerebrovascular pressure reactivity," Perspect. Med. 1-12, pp. 285-289, Sep. 2012.
Schmidt et al., "Cerebral Autoregulatory Response Depends on the Direction of Change in Perfusion Pressure," J. Neurotrauma 26, pp. 651-656, May 2009.
Ŝeverdija et al., "Assessment of dynamic cerebral autoregulation and cerebral carbon dioxide reactivity during normothermic cardiopulmonary bypass," Med. Biol. Eng. Comput. 53, pp. 195-203, Nov. 2014.
Smith, "Shedding light on the adult brain: a review of the clinical applications of near-infrared spectroscopy," Philos. Trans. R. Soc. A Math. Phys. Eng. Sci. 369, pp. 4452-4469 Oct. 2011.
Soul et al., "Fluctuating Pressure-Passivity Is Common in the Cerebral Circulation of Sick Premature Infants," Pediatric Research 61, No. 4, Nov. 2007, pp. 467-473.
Steiner, MD et al., "Continuous monitoring of cerebrovascular pressure reactivity allows determination of optimal cerebral perfusion pressure in patients with traumatic brain injury," Crit. Care Med. 30, pp. 733-738, Apr. 2002.
Steiner et al., "Near-Infrared Spectroscopy Can Monitor Dynamic Cerebral Autoregulation in Adults," Neurocrit. Care 10, pp. 122-128, Sep. 2008.
Tekes et al., "Apparent Diffusion Coefficient Scalars Correlate with Near-Infrared Spectroscopy Markers of Cerebrovascular Autoregulation in Neonates Cooled for Perinatal Hypoxic-Ischemic Injury," Am. J. Neuroradiol. 36, pp. 188-193, Jan. 2015.
Zheng et al., "Continuous Cerebral Blood Flow Autoregulation Monitoring in Patients Undergoing Liver Transplantation," Neurocrit. Care 17, pp. 77-84, Aug. 2012.
Zweifel et al., "Continuous Assessment of Cerebral Autoregulation With Near-Infrared Spectroscopy in Adults After Subarachnoid Hemorrhage," Stroke 41, pp. 1963-1968, Jan. 2010.
Zweifel et al., "Continuous time-domain monitoring of cerebral autoregulation in neurocritical care," Med. Eng. Phys. 36, 638-645, Feb. 2014.
Tsalach et al., "Cerebral Autoregulation Real-Time Monitoring," PLOS One, Aug. 29, 2016, 14 pp.
Chung MD, PhD et al., "Assessment of Noninvasive Regional Brain Oximetry in Posterior Reversible Encephalopahty Syndrome and Reversible Cerebral Vasoconstriction Syndrome," Journal of Intensive Care Medicine, vol. 31(6), Jan. 2016, pp. 415-419.
Lee et al., "Cerebrovascular Autoregulation in pediatric moyamoya Disease" Pediatric Anesthesia, 23, pp. 547-556, Jun. 2013.
Steppan, MD, et al., "Cerebral and Tissue Oximetryc" Best Pract Res Clin Anaesthesiol, Dec. 2014, pp. 429-439.
Brady et al., "A New Monitor of Pressure Autoregulation: What Does It Add?" International Anesthesia Research Society, Nov. 2015, vol. 121, No. 5, pp. 1121-1123.
Prabhakar et al., "Current concepts of optimal cerebral perfusion pressure in traumatic brain injury," J. Anaesthesiol Clin Pharmacol, Jul.-Sep. 2014, pp. 318-327.
Lang et al., "Continuous monitoring of cerebrovascular autoregulation: a validation study," J Neurol Neurosurg Psychiatry, pp. 583-586, Jan. 2002.
Lazaridis et al., Optimal cerebral perfusion pressure: are we ready for it? Neurological Research, vol. 35, No. 2, Nov. 12, 2013, pp. 138-148.
Joshi et al., "Predicting the Limits of Cerebral Autoregulation During Cardiopulmonary Bypass," Anesthesia-Analgesia, Mar. 2012, vol. 114, No. 3, pp. 503-510.
Olsen et al., "Validation of Transcranial Near-Infrared Spectroscopy for Evaluation of Cerebral Blood Flow Autoregulation," Journal of Neurosurgical Anesthesiology, pp. 280-285, Oct. 1996.
Addison et al., "Gradient adjustment method for better discriminating correlating and non-correlating regions of physiological

(56) References Cited

OTHER PUBLICATIONS signals: application to the partitioning of impaired and intact zones of cerebral autoregulation," J Clin Moit Comput, Aug. 2016, 11 pp.

Montgomery et al., "Data clustering methods for the determination of cerebral autoregulation functionality," J Clin Monit Comput, Sep. 2015, 8 pp.

Brady et al., "The Lower Limit of Cerebral Blood Flow Autoregulation is Increased with Elevated Intracranial Pressure," vol. 108, No. 4, Apr. 2009.

Gao et al., "Mathematical considerations for modeling cerebral blood flow autoregulation to systemic arterial pressure," accessed on Sep. 19, 2016, accessed from http://ajpheart.physiology.org/., pp. H1023-H1031.

Hauerberg et al., "The Upper Limit of Cerebral Blood Flow Autoregulation in Acute Intracranial Hypertension," Journal of Neurosurgical Anesthesiology, vol. 10, No. 2, pp. 106-112, May 1998.

Hori et al., "Arterial pressure above the upper cerebral autoregulation limit during cardiopulmonary bypass is associated with post-operative delirium," British Journal of Anaesthesia Sep. 2014, pp. 1009-1017.

Kamar et al., "Detecting Cerebral Autoregulation Thresholds Using a Noninvasive Cerebral Flow Monitor," Ornim medical, May 2013, Portugal Poster, 1 pp.

Lucas et al., "Influence of Changes in Blood Pressure on cerebral Perfusion and Oxygenation," Hypertension, Oct. 2009, pp. 698-705.

Minassian et al., "Changes in intracranial pressure and cerebral autoregulation in patients with severe traumatic brain injury," vol. 30, Jul. 2002, pp. 1616-1622.

Pesek, MD, et al., "The upper limit of cerebral blood flow autoregulation is decreased with elevations in intracranial pressure," Neurosurgery, vol. 75, No. 2, Aug. 2014, pp. 163-170.

Sadoshima et al., "Upper Limit of Cerebral Autoregulation During Development of Hypertension in Spontaneously Hypertensive Rats—Effect of Sympathetic Denervation," vol. 16, No. 3, May-Jun. 1985, pp. 477-481.

Sadoshima et al., "Inhibition of Angiotensin—Converting Enzyme Modulates the Autoregulation of Regional Cerebral Blood Flow in Hypertensive Rats," vol. 23, No. 6, Part 1, Jun. 1994, pp. 781-785.

Strandgaard et al., "Upper Limit of Cerebral Blood Flow Autoregulation in Experimental Renovascular Hypertension in the Baboon," vol. 37, Aug. 1975, pp. 164-167.

Ragauskas et al., "Analysis of cerebrovascular autoregulation reactivity index electronic monitoring methods," vol. 114, No. 8, Jun. 2011, 6 pp.

Chiu et al., "Assessment of cerebral autoregulation using time-domain cross-correlation analysis," Computers Bio Med, Nov. 2001, pp. 471-480.

Larson et al., "Cerebrovascular autoregulation after rewarming from hypothermia in a neonatal swine model of asphyxic brain injury," J Appl Physiol. 115; pp. 1433-1442, Sep. 2013.

Petkus et al., "Novel Method and Device for Fully Non-Invasive Cerebrovascular Autoregulation Monitoring," Elektronika Ir Elektrotechnika, vol. 20, No. 8, pp. 24-29, Oct. 2014.

Olufsen et al., "Blood pressure and blood flow variation during postural change from sitting to standing: model development and validation," J Appl Physiol Oct. 2005, pp. 1523-1537.

Rangel-Castilla, MD, et al., "Cerebral pressure autoregulation in traumatic brain injury," Neurosurg Focus, vol. 25, Oct. 2008, 8 pp.

Addison, "A Review of Wavelet Transform Time-Frequency Methods for NIRS-Based Analysis of Cerebral Autoregulation," IEEE Reviews in Biomedical Engineering, vol. 8, 2015, pp. 78-85.

Moerman, M.D., Ph.D., et al., "Assessment of Cerebral Autoregulation Patterns with Near-infrared Spectroscopy during Pharmacological-induced Pressure Changes," Anesthesiology, vol. 123, No. 2, Aug. 2015, pp. 327-335.

U.S. Appl. No. 15/911,449, naming Paul S. Addison et al. as inventors, filed Mar. 5, 2018.

U.S. Appl. No. 15/962,438, naming Paul S. Addison et al. as inventors, filed Apr. 25, 2018.

U.S. Appl. No. 15/980,235, naming Paul S. Addison et al. as inventors, filed May 15, 2018.

U.S. Appl. No. 15/962,468, naming Paul S. Addison et al. as inventors, filed Apr. 25, 2018.

U.S. Appl. No. 15/962,486, naming Dean Montgomery et al. as inventors, filed Apr. 25, 2018.

Chuan et al., "Is cerebrovascular autoregulation associated with outcomes after major noncardiac surgery? A prospective observational pilot study," Acta Anaesthesiol Scand., Aug. 5, 2018, 10 pp.

* cited by examiner

DETERMINING CHANGES TO AUTOREGULATION

TECHNICAL FIELD

This disclosure relates to physiological parameter monitoring.

BACKGROUND

In some cases, an autoregulation status of a patient may be monitored, e.g., during a medical procedure. Cerebral autoregulation (CA) is a physiological process that attempts to maintain an optimal cerebral blood flow over a wide range of blood pressure changes to supply appropriate levels of oxygen and nutrients to the brain. Complex myogenic, neurogenic, and metabolic mechanisms may be involved in CA.

During autoregulation, cerebral arterioles dilate or constrict to maintain optimal blood flow. For example, as blood pressure decreases, cerebral arterioles dilate in an attempt to maintain blood flow. As blood pressure increases, cerebral arterioles constrict to similarly maintain the blood flow that, if left unrestricted, could cause injury to the brain. Intact cerebral autoregulation function occurs over a range of blood pressures defined between a lower limit of autoregulation (LLA) and an upper limit of autoregulation (ULA). If the patient's autoregulation process is not functioning properly, then the patient may experience inappropriate cerebral blood flow, which may have an adverse effect on the patient's health. For example, a drop in cerebral blood flow may cause ischemia. As another example, an increase in cerebral blood flow may cause hyperemia, which may result in swelling of the brain or edema. Autoregulation dysfunction may result from a number of causes including, stroke, traumatic brain injury, brain lesions, brain asphyxia, or infections of the central nervous system.

SUMMARY

This disclosure describes devices, systems, and techniques for determining a change in autoregulation, such as a change to one or more limits indicating intact cerebral autoregulation. An example regional oximetry device may determine an expected value and an actual value of a physiological parameter at a particular blood pressure value of a patient. The regional oximetry device may determine the expected value based on a first relationship between the blood pressure of the patient and the physiological parameter of the patient. The regional oximetry device of this disclosure is configured to determine a second relationship based on the difference between the actual value and the expected value. For example, the difference may indicate that one or both of the limits of autoregulation of the patient have shifted to higher or lower blood pressure values. The shifted limits of autoregulation may therefore indicate updated blood pressure values that indicate intact cerebral autoregulation for the patient.

Clause 1: In some examples, a device comprises a memory configured to store a first relationship between a blood pressure of a patient and a physiological parameter of the patient, the physiological parameter being different than the blood pressure, the first relationship being indicative of cerebral autoregulation of the patient. The device also comprises processing circuitry configured to receive a first physiological signal indicative of the blood pressure of the patient and a second physiological signal indicative of the physiological parameter of the patient. The processing circuitry is also configured to determine, based on the first relationship, an expected value of the physiological parameter at a particular blood pressure value of the first physiological signal. The processing circuitry is further configured to determine an actual value of the physiological parameter from the second physiological signal at the particular blood pressure value of the first physiological signal and determine a difference between the actual value of the physiological parameter and the expected value of the physiological parameter. The processing circuitry is configured to determine, based on the difference between the actual value and the expected value, a second relationship between the blood pressure of the patient and the physiological parameter of the patient, the second relationship being indicative of a change in the cerebral autoregulation of the patient from the first relationship. The processing circuitry is configured to store, in the memory, the second relationship between the blood pressure of the patient and the physiological parameter of the patient.

Clause 2: In some examples of clause 1, the processing circuitry is further configured to determine two or more expected values of the physiological parameter at two or more respective blood pressure values of the first physiological signal and determine two or more actual values of the physiological parameter from the second physiological signal at the two or more respective blood pressure values of the first physiological signal. The processing circuitry is also configured to determine a collective difference between the two or more actual values of the physiological parameter and the two or more expected values of the physiological value, wherein the processing circuitry is configured to determine the second relationship between the blood pressure of the patient and the physiological parameter of the patient based on the collective difference.

Clause 3: In some examples of clause 1 or clause 2, the processing circuitry is further configured to determine whether the second relationship has a higher expected value of the physiological parameter or a lower expected value of the physiological parameter than the first relationship at the particular blood pressure value. The processing circuitry is also configured to determine a change in a limit of cerebral autoregulation based on whether the second relationship has the higher expected value or the lower expected value of the physiological parameter at the particular blood pressure value.

Clause 4: In some examples of any of clauses 1-3, the processing circuitry is configured to determine the second relationship by at least determining an updated estimate of a limit of cerebral autoregulation with respect to the blood pressure of the patient. The updated estimate of the limit of cerebral autoregulation is associated with the second relationship, and the updated estimate of the limit of cerebral autoregulation is different from a previous estimate of the limit of cerebral autoregulation associated with the first relationship Clause 5: In some examples of clause 4, the updated estimate of the limit of cerebral autoregulation is an updated estimate of a first limit of cerebral autoregulation, and the previous estimate of the limit of cerebral autoregulation is a previous estimate of the first limit of cerebral autoregulation. The processing circuitry is further configured to determine, based on a difference between the updated estimate of the first limit of cerebral autoregulation and the previous estimate of the first limit of cerebral autoregulation, a change in a second limit of cerebral autoregulation.

Clause 6: In some examples of any of clauses 1-5, the device further comprises a display, and the processing circuitry is further configured to determine the change in the cerebral autoregulation by at least determining an amplitude of change between a previous estimate of the limit of cerebral autoregulation and an updated estimate of the limit of cerebral autoregulation and present an indication of the amplitude of change in the limit of cerebral autoregulation.

Clause 7: In some examples of any of clauses 1-6, the device further comprises a display, and the processing circuitry is further configured to present, via the display, an indication of the second relationship.

Clause 8: In some examples of clause 7, the processing circuitry is further configured to determine a cerebral autoregulation status of the patient based on the second relationship and the blood pressure of the patient and present, via the display, an indication of the cerebral autoregulation status.

Clause 9: In some examples of clause 8, the processing circuitry is further configured to determine a change in a limit of cerebral autoregulation in response to determining the second relationship and present, via the display, an indication of the cerebral autoregulation status as a color. The processing circuitry is also configured to change the intensity of the color in response to determining the change in the limit of cerebral autoregulation.

Clause 10: In some examples of clause 9, the processing circuitry is configured to change the intensity of the color by at least changing the intensity of the color based on a magnitude of the change in the limit of cerebral autoregulation.

Clause 11: In some examples of any of clauses 1-10, the processing circuitry is further configured to determine a target blood pressure based on the first physiological signal and determine a change in the target blood pressure based on a change in the first physiological signal. The processing circuitry is configured to, responsive to determining the change in the target blood pressure, determine, based on the change in the target blood pressure, the second relationship and at least one of an updated estimate of a lower limit of cerebral autoregulation or updated estimate of an upper limit of cerebral autoregulation.

Clause 12: In some examples of clause 11, the device further comprises a display, and the processing circuitry is further configured to, responsive to determining the change in the cerebral autoregulation from the first relationship to the second relationship, generate an alert representative of the change in the cerebral autoregulation and present, via the display, the alert.

Clause 13: In some examples of any of clauses 1-12, the physiological parameter comprises a confidence in a metric representative of the cerebral autoregulation of the patient.

Clause 14: In some examples of any of clauses 1-13, the processing circuitry is further configured to determine that the difference between the actual value and the expected value is greater than a threshold value and, responsive to determining that the difference between the actual value and the expected value is greater than the threshold value instead of less than the threshold value, determine the second relationship between the blood pressure of the patient and the physiological parameter of the patient.

Clause 15: In some examples, a method comprises storing, in a memory, a first relationship between a blood pressure of a patient and a physiological parameter of the patient, the physiological parameter being different than the blood pressure, the first relationship being indicative of cerebral autoregulation of the patient. The method also comprises receiving a first physiological signal indicative of the blood pressure of the patient and a physiological signal indicative of the physiological parameter of the patient. The method further comprises determining, based on the first relationship, an expected value of the physiological parameter at a particular blood pressure value of the first physiological signal and determining an actual value of the physiological parameter from the second physiological signal at the particular blood pressure value of the first physiological signal. The method comprises determining a difference between the actual value of the physiological parameter and the expected value of the physiological parameter. The method also comprises determining, based on the difference between the actual value and the expected value, a second relationship between the blood pressure of the patient and the physiological parameter of the patient, the second relationship being indicative of a change in the cerebral autoregulation of the patient from the first relationship. The method further comprises storing, in the memory, the second relationship between the blood pressure of the patient and the physiological parameter of the patient.

Clause 16: In some examples of clause 15, the method further comprises determining two or more expected values of the physiological parameter at two or more respective blood pressure values of the first physiological signal. The method also comprises determining two or more actual values of the physiological parameter from the second physiological signal at the respective two or more blood pressure values of the first physiological signal. The method comprises determining a collective difference between the two or more actual values of the physiological parameter and the two or more expected values of the physiological value, wherein determining the second relationship between the blood pressure of the patient and the physiological parameter of the patient is based on the collective difference.

Clause 17: In some examples of clause 15 or 16, the method further comprises determining whether the second relationship has a higher expected value of the physiological parameter or a lower expected value of the physiological parameter than the first relationship at the particular blood pressure value. The method also comprises determining a change in a limit of cerebral autoregulation based on whether the second relationship has the higher expected value or the lower expected value of the physiological parameter at the particular blood pressure value.

Clause 18: In some examples of any of clauses 15-17, the method further comprises determining a change in a limit of cerebral autoregulation in response to determining the second relationship and determining a cerebral autoregulation status of the patient based on the second relationship and the blood pressure of the patient. The method also comprises presenting, via the display, an indication of the cerebral autoregulation status as a color and changing the intensity of the color in response to determining the change in the limit of cerebral autoregulation.

Clause 19: In some examples of any of clauses 15-18, the method further comprises determining a target blood pressure based on the first physiological signal and determining a change in the target blood pressure based on a change in the first physiological signal, wherein determining the second relationship is responsive to determining the change in the target blood pressure.

Clause 20: In some examples, a device comprises a display and a memory configured to store a first relationship between a blood pressure of a patient and a physiological parameter of the patient, the physiological parameter being different than the blood pressure, the first relationship being indicative of cerebral autoregulation of the patient. The device also comprises sensing circuitry configured to receive a first physiological signal indicative of the blood pressure of the patient and a second physiological signal indicative of the physiological parameter of the patient. The device further comprises processing circuitry configured to determine, based on the first relationship, an expected value of the physiological parameter at a particular blood pressure value of the first physiological signal. The processing circuitry is further configured to determine an actual value of the physiological parameter from the second physiological signal at the particular blood pressure value of the first physiological signal and determine a difference between the actual value of the physiological parameter and the expected value of the physiological parameter. The processing circuitry is configured to determine, based on the difference between the actual value and the expected value, a second relationship between the blood pressure of the patient and the physiological parameter of the patient, the second relationship being indicative of a change in the cerebral autoregulation of the patient from the first relationship. The processing circuitry is configured to determine a lower limit of cerebral autoregulation and an upper limit of cerebral autoregulation based on the second relationship, wherein blood pressure values between the lower limit of cerebral autoregulation and the upper limit of cerebral autoregulation indicate a blood pressure range representative of intact cerebral autoregulation for the patient. The processing circuitry is further configured to present, via the display, an indication of the cerebral autoregulation status based on the lower limit of cerebral autoregulation and the upper limit of cerebral autoregulation and store, in the memory, the second relationship between the blood pressure of the patient and the physiological parameter of the patient.

The details of one or more examples are set forth in the accompanying drawings and the description below. Other features, objects, and advantages will be apparent from the description and drawings, and from the claims.

DETAILED DESCRIPTION

Figure 1:
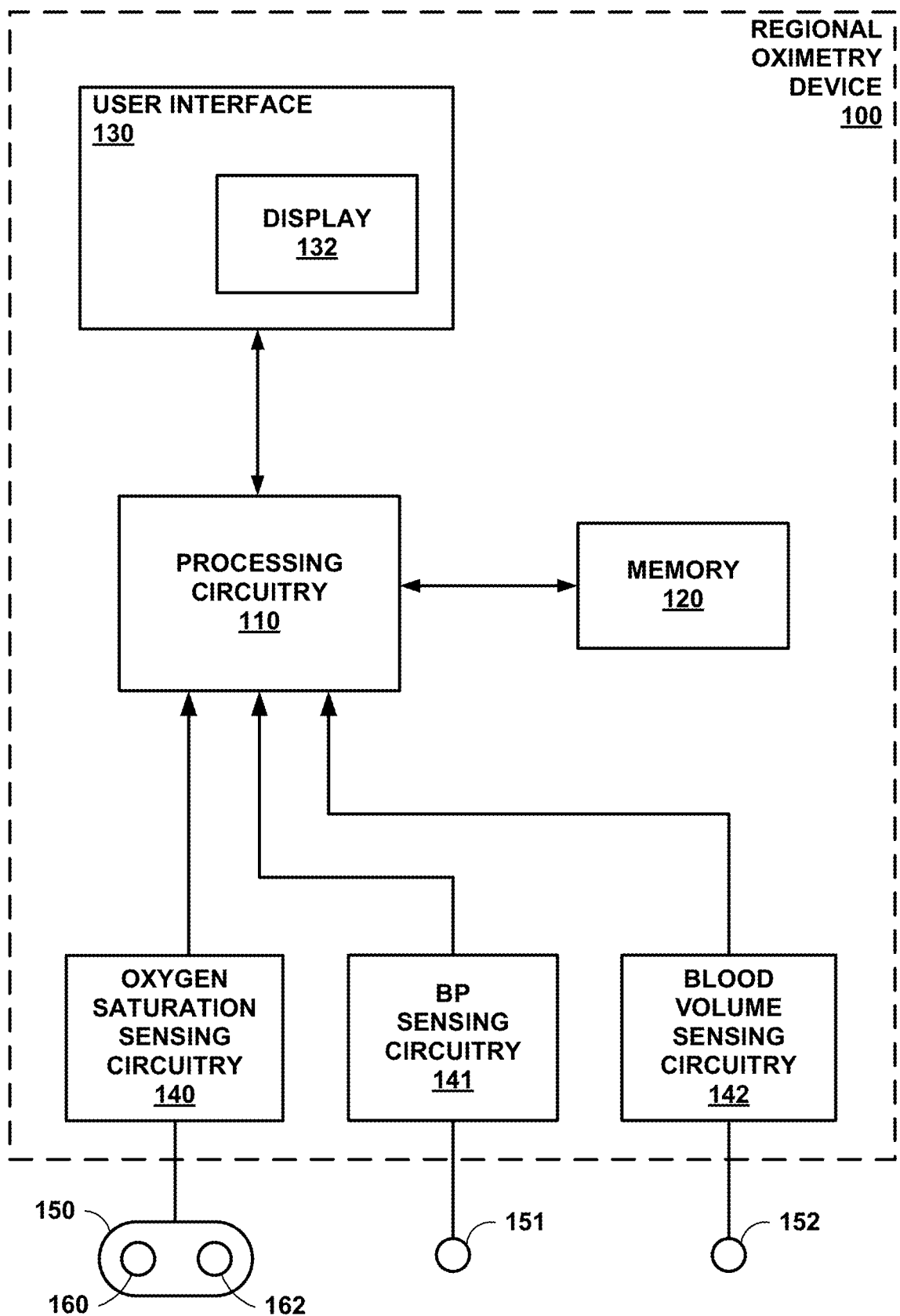
FIG. 1 is a conceptual block diagram illustrating an example regional oximetry device.

This disclosure describes devices, systems, and techniques for determining changes in cerebral autoregulation (CA) of a patient. The autoregulation status of a patient may be an indication that the cerebral autoregulation control mechanism of the patient is intact (e.g., functioning properly) or impaired (e.g., not functioning properly). A CA control mechanism of the body may regulate cerebral blood flow (CBF) over a range of systemic blood pressures. This range of systemic blood pressures may lie within a lower limit of autoregulation (LLA) and an upper limit of autoregulation (ULA). Outside of the LLA and the ULA, blood pressure directly drives CBF, and CA function may thus be considered impaired.

One method to determine the limits of autoregulation (e.g., the LLA and ULA) noninvasively using near-infrared spectroscopy (NIRS) technology may include the cerebral oximetry index (COx) measure, which is a moving correlation index between mean arterial pressure (MAP) and regional oxygen saturation ($rSO_2$). The COx measure (e.g., the Pearson coefficient) is derived from the correlation between $rSO_2$ and MAP. COx relates to the regression line fit or linear correlation between $rSO_2$ and MAP over a time window, such as three hundred seconds in some examples. The COx method may be used to produce a representation of a patient's blood-pressure-dependent autoregulation status. When the CA is intact for a patient, there is typically no correlation between MAP and $rSO_2$. In contrast, MAP and $rSO_2$ typically directly correlate (e.g., the correlation index of COx is approximately 1) when the CA is impaired. In practice, however, sensed data indicative of autoregulation may be noisy and/or there might be a slightly correlated relationship between variables (e.g., MAP and $rSO_2$) even when CA is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In addition, a patient state, which may include the current state of CA of the patient, as indicated by sensed physiological signals, may change quickly over time. In response to a changing patient state, a limit of autoregulation may change quickly, which changes the boundaries of acceptable sensed physiological signal values used by a clinician to track the status of a patient. However, the processing circuitry may not necessarily determine the change until the processing circuitry has obtained a significant amount of data. In some examples, the slowly changing estimate will be inaccurate during a time interval after the change in patient state. Other possible causes of large differences between estimates of limits of cerebral autoregulation include electrocautery, damping of blood pressures due to catherization of the patient, changes in sensed blood pressure due to probe (e.g., sensor) movement relative to the patient, and changes in sensed blood pressure due to line flushing.

A system may not be able to identify changes in limits of cerebral autoregulation unless the blood pressure of the patient crosses one of the limits. The system may use data from past crossings of the limits of cerebral autoregulation to determine the blood pressure values of the limits of cerebral autoregulation. However, if the limits of cerebral autoregulation have changed since the last crossing, the system may not be able to detect the change because the blood pressure may not cross one of the limits. If a system is not able to appropriately identify and update changing limits of cerebral autoregulation for the patient, the clinician may be monitoring the patient using physiological information that is not representative of the current patient state.

As described herein, a system may monitor physiological signals sensed from the patient to identify changes to autoregulation and change the limits used to define an intact autoregulation system of the patient. The system may include a regional oximetry device including processing circuitry configured to determine and store a relationship between a blood pressure of the patient and a physiological parameter of the patient. In some examples, the physiological parameter includes oxygen saturation, blood volume under sensor (BVS), hemoglobin volume index (HVx), or a correlation coefficient between blood pressure and oxygen saturation of the patient. The physiological parameter may also be the confidence in a CA metric. The processing circuitry may be configured to determine an expected value of the physiological parameter at a particular blood pressure value based on the relationship.

In order to determine a change in the CA of the patient, the processing circuitry is configured to determine a difference between an actual value of the physiological parameter and the expected value. The processing circuitry may determine the actual value of the physiological parameter in real time based on a physiological signal received by the processing circuitry. The difference between the actual value and the expected value may indicate that the relationship between the blood pressure of the patient and the physiological parameter has shifted to higher or lower blood pressure values.

The devices, systems, and techniques of this disclosure may allow faster determinations of changes in CA of patients. For example, another device may determine a change in CA based on recent measurements of blood pressure and oxygen saturation. The other device may determine correlation coefficients (e.g., correlation indices) based on the blood pressure and oxygen saturation measurements and then determine the limits of cerebral autoregulation based on the correlation coefficients. Determining a large set of correlation coefficients may take a relatively long amount of time (e.g., one to five minutes), whereas determining a difference between an actual value and an expected value may be completed using less data and in less time (e.g., less than five or ten seconds).

Processing circuitry implementing the devices, systems, and techniques of this disclosure may present an improved graphical user interface with more accurate information relating to the CA of the patient. The processing circuitry may present a clinician with an indication of a change in CA faster than another device that does not determine an updated relationship between the blood pressure of a patient and a physiological parameter of the patient based on the difference between an expected value and an actual value of the physiological parameter at a particular blood pressure. Therefore, the systems and techniques described herein may be configured to sense physiological signals that may change relatively rapidly over time due to physiological effects during a medical procedure, drugs, or other factors. If the processing circuitry determines an autoregulation status of a patient based on stored relationship between blood pressure and a physiological parameter is no longer accurate, then the system may use more current sensed information to update the determined autoregulation status and present updated limits to autoregulation for viewing by a clinician.

FIG. 1 is a conceptual block diagram illustrating an example regional oximetry device 100. Regional oximetry device 100 includes processing circuitry 110, memory 120, user interface 130, display 132, sensing circuitry 140, 141, and 142, and sensing device(s) 150, 151, and 152. In some examples, regional oximetry device 100 may be configured to determine and display the cerebral autoregulation status of a patient, e.g., during a medical procedure or for more long-term monitoring, such as monitoring of prenatal infants, children, or adults. A clinician may receive information regarding the cerebral autoregulation status of a patient via display 132 and adjust treatment or therapy to the patient based on the cerebral autoregulation status information.

Processing circuitry 110 as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of blood pressure, oxygen saturation, blood volume, other physiological parameters, relationships between blood pressure and physiological parameters, MAP values, $rSO_2$ values, COx values, BVS values, HVx values, and/or value(s) of an LLA and/or a ULA, for example. Memory 120 may also be configured to store data such as relationships between blood pressure and other physiological parameters and expected values of physiological parameters. Memory 120 may also be configured to store data such as threshold levels for physiological parameters, threshold values for blood pressure, and/or threshold levels for signal quality metrics. The relationships and expected values may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, physiological parameter values, and indications of cerebral autoregulation status of a patient via display 132. In some examples, if processing circuitry 110 determines that the cerebral autoregulation status of the patient is impaired, then processing circuitry 110 may present a notification (e.g., an alert) indicating the impaired cerebral autoregulation status via display 132. As another example, processing circuitry 110 may present, via display 132, estimates of rSO$_2$ for a patient, an estimate of the blood oxygen saturation (SpO$_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. User interface 130 may also include means for projecting audio to a user, such as speaker(s). Processing circuitry 110 may be configured to present, via user interface 130, a visual, audible, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor).

Sensing circuitry 140, 141, and 142 may be configured to receive physiological signals sensed by respective sensing device(s) 150, 151, and 152 and communicate the physiological signals to processing circuitry 110. Sensing device(s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, heart rate, and respiration. Sensing circuitry 140, 141, and 142 may include, but are not limited to, blood pressure sensing circuitry, oxygen saturation sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160 (these multiple detectors are shown as a single detector in the example of FIG. 1). Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may physically separate from each other and separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's cerebral autoregulation status.

Processing circuitry 110 may be configured to receive one or more physiological signals generated by sensing devices 150, 151, and 152 and sensing circuitry 140, 141, and 142. The physiological signals may include a signal indicating blood pressure, a signal indicating oxygen saturation, and/or a signal indicating blood volume of a patient. Processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value, a gradient-based metric of two or more physiological parameters, and/or another physiological parameter. Processing circuitry 110 can determine a gradients-based metric by determining respective gradients of signals for physiological parameters and determining whether the respective gradients trend together. Processing circuitry 110 may also be configured to determine an expected value of the physiological parameter based on the relationship and an actual value of the physiological parameter based on a physiological signal received by sensing circuitry 140, 141, and 142. As discussed in further detail below with respect to FIGS. 5 and 6, processing circuitry 110 may determine a difference between one or more actual values and one or more expected values of the physiological parameter of the patient.

Processing circuitry 110 may be configured to determine a relationship between blood pressure values and a physiological parameter of a patient using any suitable technique. For example, processing circuitry 110 may be configured to determine a trendline or a polynomial function to fit or match data points, where each data point represents a physiological parameter value and a respective blood pressure value. Processing circuitry 110 stores the relationship to memory 120 as a function, trendline, curve, algorithm, and/or any other relationship format. Processing circuitry 110 may then be configured to determine one or more expected values of the physiological parameter at one or more particular blood pressure values based on the stored relationship.

As described further herein, the expected values of the physiological parameter determined by processing circuitry 110 may not necessarily match the past measured values of the physiological parameter or the actual, future values of the physiological parameter. Although processing circuitry 110 determines the stored relationship based on the past measured values, the relationship may not perfectly fit the past measured values of the physiological parameter. As an example, the past measured values of the physiological parameter can include two different values of the physiological parameter at the same particular blood pressure value. The stored relationship may define expected values of the physiological parameter based on a function (e.g., a polynomial), which may define a single expected value of the physiological parameter for each input blood pressure value. Therefore, at least one of the past measured values of the physiological parameter may be different than the expected value on the curve or trendline of the stored relationship function. In order to determine a relationship that is a "best match" to the past measured values, processing circuitry 110 may choose a function or curve that does not exactly match some or all of the data points.

After processing circuitry 110 determines and stores the relationship to memory 120, processing circuitry 110 determines new, actual values of the physiological parameter, along with corresponding or associated blood pressure values. Processing circuitry 110 may determine the new, actual values based on new physiological signals from sensing devices 150, 151, and 152. Processing circuitry 110 may be configured to determine actual values of the physiological parameter and blood pressure with a slight delay due to the propagation of the physiological signals through devices 150, 151, and 152, and/or circuitries 140, 141, and 142. In addition, there may be a delay associated with the processing and analysis of the physiological signals by devices 150, 151, and 152, circuitries 140, 141, and 142, and/or processing circuitry 110.

The actual values of the physiological parameter may differ from the expected values of the physiological parameter determined by processing circuitry 110 based on the stored relationship. In some examples, the difference between the actual values and the expected values may indicate a shift in the CA of the patient. Additionally, or alternatively, the difference may be due to noise or normal fluctuations of the physiological signals. A relatively large difference between the one or more actual values and the one or more expected values may indicate a change in CA, while a relatively small difference or no difference may indicate no change in the CA. Since the shift in the CA may indicate that intact autoregulation falls within different values of a physiological signal (e.g., a different range of blood pressure values), processing circuitry 110 may determine these different limits to autoregulation and present them to the clinician via user interface 130 to inform the clinician of the change.

Processing circuitry 110 may determine an updated version of the relationship (e.g., a second relationship) based on the difference between one or more expected values of the physiological parameter and the one or more actual values of the physiological parameter. Processing circuitry 110 can make this determination even when all of the recent measured blood pressure values are between the estimates of the limits of cerebral autoregulation. In some examples, processing circuitry 110 may be configured to determine whether the difference exceeds a threshold value and only determine a new relationship if the difference exceeds the threshold value. The difference between the expected values and the actual values may be a collective difference based on multiple individual differences between expected values and the actual values. The collective difference may be the sum or average of the individual differences. In some examples, processing circuitry 110 may also use the standard deviation or variance of the individual differences to decide whether to determine an updated version of the relationship between the physiological parameter and the blood pressure values. In some examples, the collective difference between expected values and actual values may be represented as a difference between two curves defines by the respective expected values and actual values to identify the change between the two curves. Processing circuitry 110 may assign more weight or confidence to a collective difference based on a larger number of data points because a single data point may not always accurately indicate a change in the CA of a patient.

Processing circuitry 110 may be configured to determine an updated version of the relationship by shifting the previous version of the relationship to higher or lower blood pressure values, as shown in Equation (1). Processing circuitry 110 may use a transformation function f(x) as shown in Equation (2) to determine an updated relationship based on the previous version. Processing circuitry 110 may also use scaling to amplify the expected values of the physiological parameter, as shown in Equation (3), and/or scaling to effectively stretch or compress the relationship function, as shown in Equation (4). Alternatively, processing circuitry 110 may determine a new version relationship without using the previous version of the relationship, as shown in Equation (5) for the example of a polynomial relationship. For the updated version of the relationship, processing circuitry 110 may re-determine the constants of the polynomial function. Equations (3)-(5) are specific examples of Equation (2), although other examples are possible. Processing circuitry 110 may be configured to determine the updated version of the relationship as a general function of the previous version of the relationship, as shown in Equation (6).

After determining the updated version of the relationship, processing circuitry 110 stores the updated version of the relationship to memory 120. In Equations (1)-(6), $r_1(x)$ represents the previous version of the relationship, $r_2(x)$ represents the updated version of the relationship, A-G and n are constants. x and $x_0$ are expressed in terms of blood pressure units such as millimeters of mercury (mmHg), and $r_1$ and $r_2$ produce values in terms of the units of the physiological parameter. f(x) and g(x) are functions, such as linear functions, polynomial functions, trigonometric functions, exponential functions, logarithmic functions, and/or any other type of functions.

$$r_2(x)=Ar_1(x)+B \quad (1)$$

$$r_2(x)=r_1(f(x)) \quad (2)$$

$$r_2(x)=r_1(x-x_0) \quad (3)$$

$$r_2(x)=r_1(Cx) \quad (4)$$

$$r_2(x)=r_1(Dx^n+\ldots+Ex^2+Fx+G) \quad (5)$$

$$r_2(x)=g(r_1(x)) \quad (6)$$

Processing circuitry 110 may use the stored relationship to determine a CA status for the patient. Processing circuitry 110 may be configured to determine the blood pressure values for which the physiological parameter is less than or greater than one or more threshold values. As an example, processing circuitry 110 may determine an estimate of the lower limit of cerebral autoregulation based on the lowest blood pressure value at which the expected value of COx is less than a threshold value, such as 0.5, 0.4, 0.3, 0.2, 0.1, or 0.0. Thus, processing circuitry 110 may determine updated estimates of the limits of cerebral autoregulation (e.g., the LLA and the ULA) based on the updated version of the relationship. Additional example details of determining LA's and cerebral autoregulation status may be found in commonly assigned U.S. Patent Application Publication No. 2018/0014791 filed on Jul. 13, 2017, and entitled "Systems and Methods of Monitoring Autoregulation," and commonly assigned U.S. Provisional Patent Application No. 62/510,303 filed on May 24, 2017, and entitled "Determining a Limit of Autoregulation," the entire contents of each of which are incorporated herein by reference.

Processing circuitry 110 may be configured to determine that the patient has an intact CA based on determining that a most recent blood pressure value of the patient is between the upper and lower limits of cerebral autoregulation. Thus, by determining a change in the CA of the patient, processing circuitry 110 may provide a more accurate determination of the CA status of the patient. The limits of cerebral autoregulation of a patient may shift over time, so a relatively quick and accurate determination of changes in CA improves the presentation of CA status and limits of cerebral autoregulation via user interface 130 to a clinician. In some examples, processing circuitry 110 is configured to display blood pressure values, measured values of the physiological parameter, and/or the CA status of a patient, for example, in real-time or nearly in real-time (e.g., with less than one second delays), via display 132.

Figure 2:
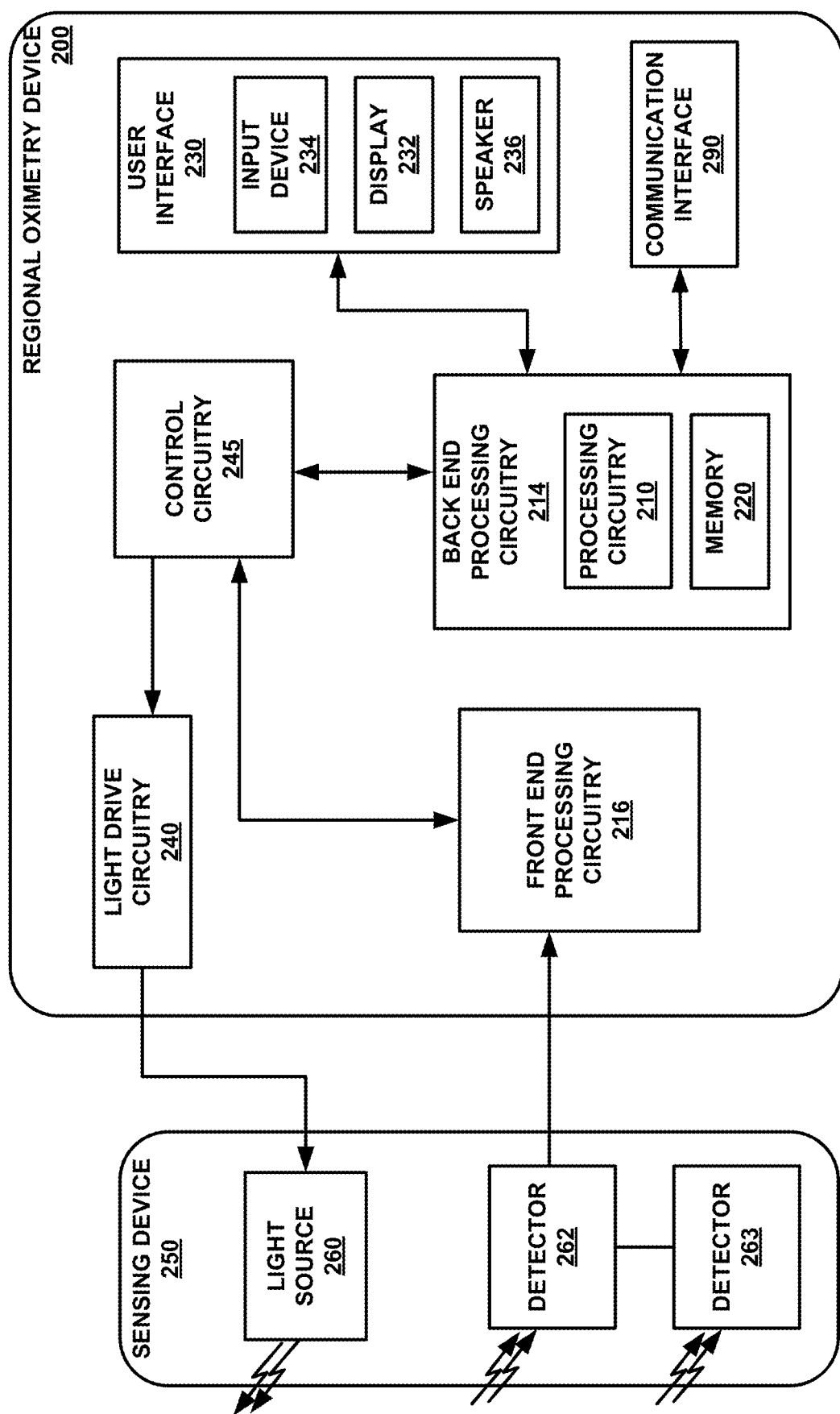
FIG. 2 is a conceptual block diagram illustrating an example regional oximetry device configured to monitor the autoregulation status of a patient.

FIG. 2 is a conceptual block diagram illustrating an example regional oximetry device 200 configured to monitor the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths (e.g., up to four or more wavelengths) of light (e.g., red and infrared (IR)) into a subject's tissue. For example, light source 260 may include a red light emitting light source and an IR light emitting light source, (e.g., red and IR LEDs), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, which may process the detection signals and determine physiological parameters (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110 of FIG. 1. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters. Processing circuitry 210 is also configured to determine a cerebral autoregulation status based on a determined change in a relationship between the blood pressure of a patient and another physiological parameter of the patient. Processing circuitry 210 can determine a change in the relationship by determining a difference between an expected value determined from a previous version of the relationship and an actual value of the physiological parameter.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store a relationship between blood pressure and a physiological parameter, and so on. Back-end processing circuitry 214 may be communicatively coupled with user interface 230 and communication interface 290.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include one or more of any type of user input device such as a keyboard, a mouse, a touch screen, buttons, switches, a microphone, a joy stick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine the type of presentation for display 232 based on user inputs received by input device 234. For example, processing circuitry 210 may be configured to present, via display 232, graphical user interface 300 shown in FIG. 3 or graph 400 shown in FIG. 4.

Figure 3:
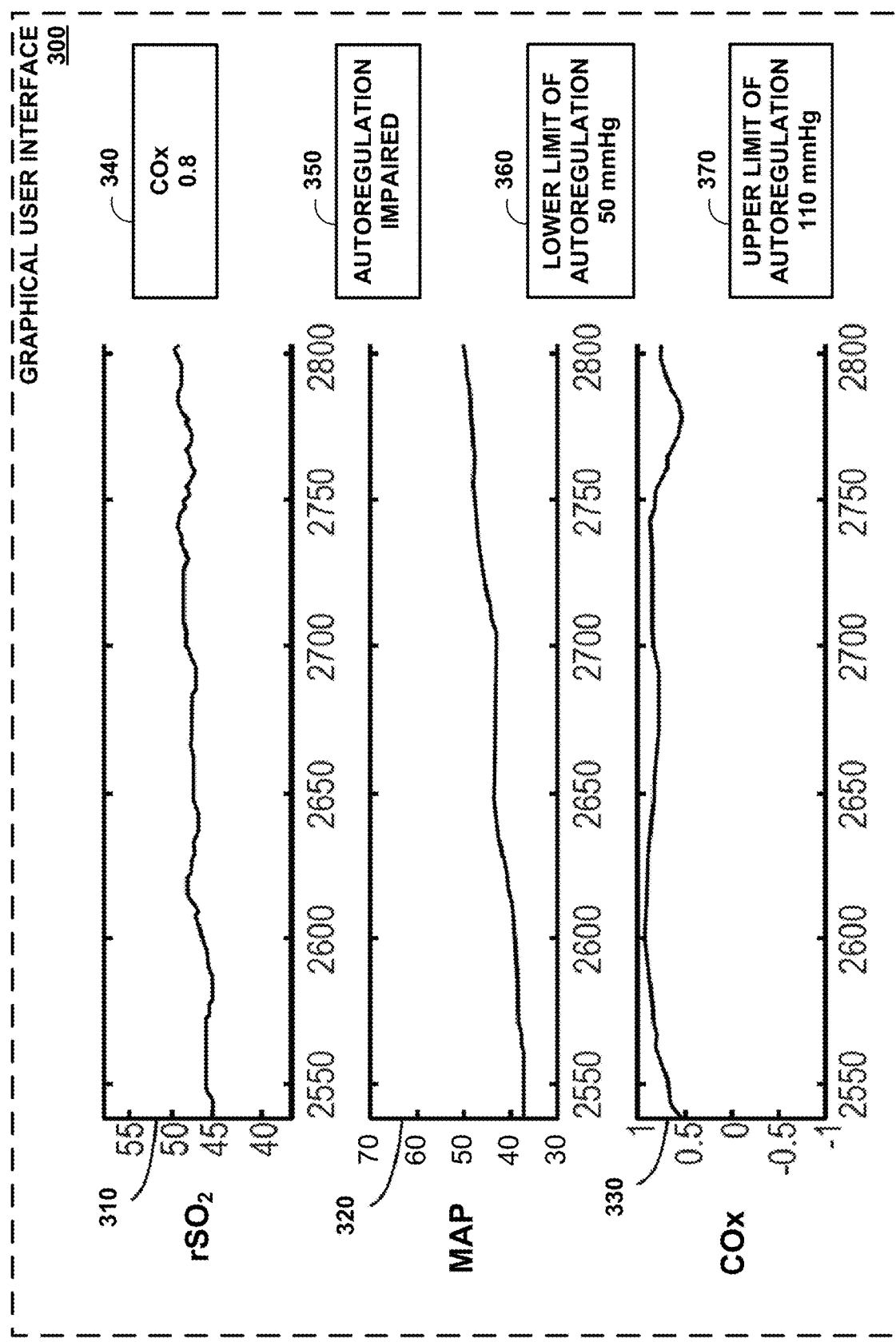
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "rSO$_2$" measurement). Display 232 may also present indications of the upper and lower limits of cerebral autoregulation. Speaker 236 within user interface 230 may provide an audible sound that may be used in various examples, such as for example, sounding an audible alarm in the event that a patient's physiological parameters are not within a predefined normal range.

Communication interface 290 may enable regional oximetry device 200 to exchange information with other external or implanted devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIGS. 3-6 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 3-6.

Graphical user interface 300 may be configured to display various information related to blood pressure, oxygen saturation, the COx index, limits of cerebral autoregulation, and/or cerebral autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

COx value indicator 340 shows a COx value of 0.8, which may result in a determination by processing circuitry 110 that the cerebral autoregulation status of the patient is impaired. Processing circuitry 110 may be configured to present, as the COx value in COx value indicator 340, the most recently determined COx value. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. Processing circuitry 110 can present text such as "intact" or "impaired" in autoregulation status indicator 350. Processing circuitry 110 can also present a color such as green (e.g., for intact cerebral autoregulation) or red (e.g., for impaired cerebral autoregulation).

Processing circuitry 110 may present limit of autoregulation indicators 360 and/or 370 in terms of blood pressure, for example, millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine the cerebral autoregulation status for presentation in autoregulation status indicator 350 by comparing the most recently determined MAP value to the limits of cerebral autoregulation. For example, if processing circuitry 110 estimates the lower limit of cerebral autoregulation at 50 mmHg and determines a MAP value at 40 mmHg, processing circuitry 110 may determine that the cerebral autoregulation status of the patient is impaired, or not intact. In response to determining that the MAP value is less than or equal to the estimate of the lower limit of cerebral autoregulation for more than the predetermined period of time, processing circuitry 110 may output a notification in autoregulation status indicator 350 as text, color, blinking, and/or any other suitable visible or audible manner.

Figure 4:
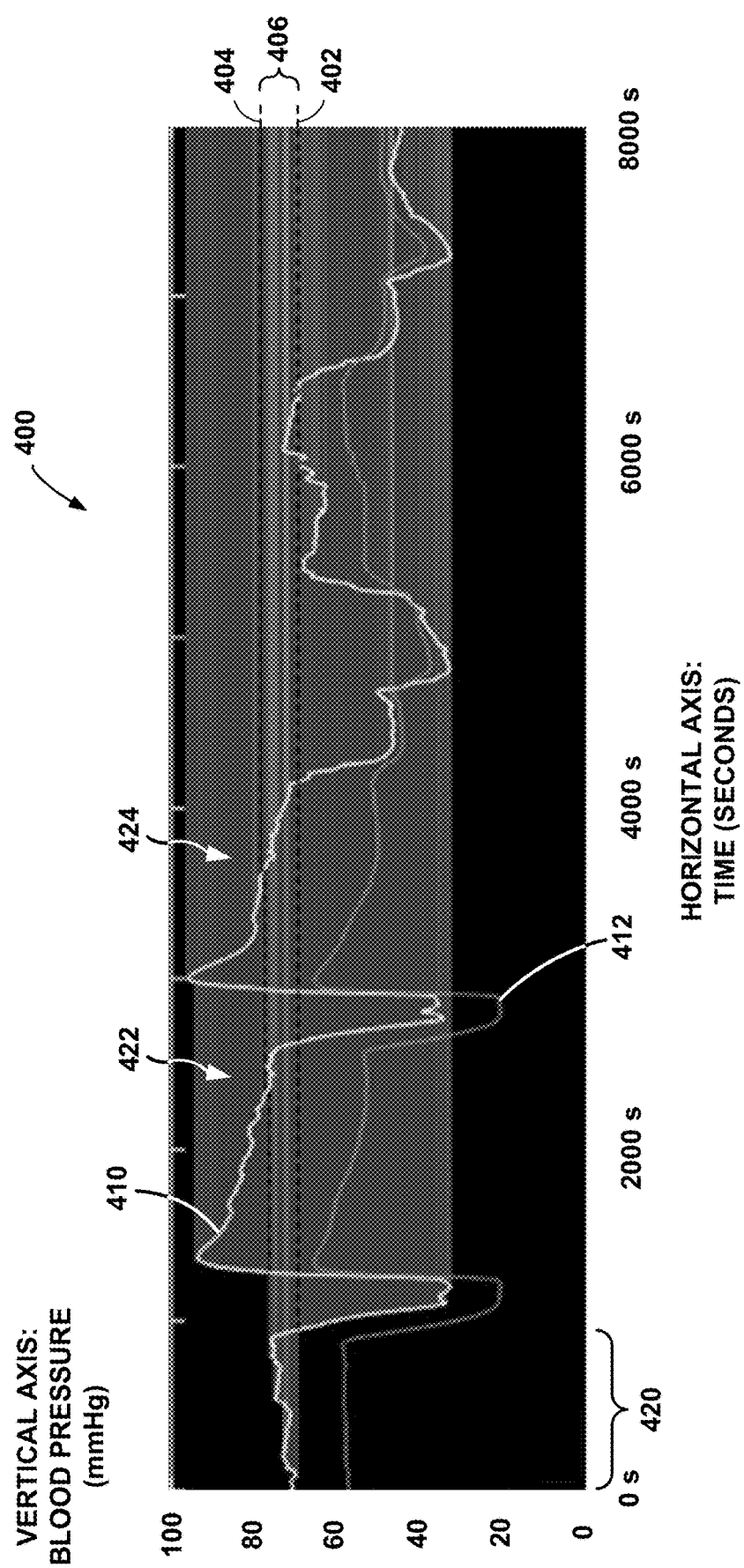
FIG. 4 is a graph illustrating blood pressure over time along with the lower and upper limits of autoregulation, in accordance with some examples of this disclosure.

FIG. 4 is a graph 400 illustrating blood pressure over time along with the lower and upper limits of cerebral autoregulation 402 and 404 (e.g., LLA 402 and ULA 404), in accordance with some examples of this disclosure. Graph 400 is an example of a presentation of limits of cerebral autoregulation 402 and 404 and a cerebral autoregulation status by processing circuitry 110 or 214 via display 132 or 232. Processing circuitry 110 can also present graph 400 on, e.g., graphical user interface 300.

Processing circuitry 110 can generate and present graph 400 to show blood pressure line 410 of a patient over time, along with the estimates of the limits of cerebral autoregulation 402 and 404. Processing circuitry 110 can also generate oxygen saturation line 412 of the patient over time. Processing circuitry 110 can also present an indication of cerebral autoregulation status in graph 400 by, for example, presenting blood pressure line 410 between or outside of LLA 402 and ULA 404. Intact area of cerebral autoregulation 406 exists between ULA 402 and ULA 404.

In some examples, processing circuitry 110 is configured to present intact area of cerebral autoregulation 406 between ULA 402 and ULA 404 as a green color (e.g., an intact region of cerebral autoregulation). Processing circuitry 110 can also present the region of graph 400 above ULA 404 and the region below LLA 402 as red colors (e.g., impaired regions of cerebral autoregulation) which may or may not be different shades of red, for example. In response to determining a change in the relationship between a blood pressure and another physiological parameter of a patient, processing circuitry 110 can move the lines associated with LLA 402 and/or ULA 404. Therefore, intact area of cerebral autoregulation 406 may change position up or down and/or change the size.

In some examples, processing circuitry 110 is configured to present an indication of the cerebral autoregulation status as a color, such as green or red. Processing circuitry 110 may present the color on a graphical user interface such as graph 400 or graphical user interface 300 shown in FIG. 3. Processing circuitry 110 may be configured to change the intensity of the color(s) in response to determining a change in a limit of cerebral autoregulation. Processing circuitry 110 can change the intensity of the color based on the magnitude of the determined change in the limit of cerebral autoregulation. For example, in response to determining a relatively large change in a limit of cerebral autoregulation, processing circuitry 110 may significantly reduce the intensity of the green color presented in intact area of cerebral autoregulation 406. The less intense green color may indicate lower confidence in the estimates of limits of cerebral autoregulation 402 and 404.

In response to determining a relatively small change in the limit of cerebral autoregulation, processing circuitry 110 may slightly reduce the intensity of the green color presented in intact area of cerebral autoregulation 406. In response to determining no change in the limit of cerebral autoregulation, processing circuitry 110 may not change or may increase the intensity of the green color presented in intact area of cerebral autoregulation 406. Thus, with respect to intact area of cerebral autoregulation 406, a large change may result in a much dimmer green color, a small change may result in a slightly dimmer green color, and no change may result in a brighter green color or no change in the green color. Processing circuitry 110 may use similar techniques to change the red color in the impaired areas of cerebral autoregulation in graph 400.

In response to determining a change in the cerebral autoregulation of a patient, processing circuitry 110 may change the intensity of the colors for previous times in graph 400. For example, processing circuitry 110 can make the colors for times before the determined change in cerebral autoregulation less intense. Processing circuitry 110 may use the normal or default color intensity for times after the determined change. In response to determining a change in cerebral autoregulation at 4,000 seconds on graph 400, processing circuitry 110 can dim the green and red colors for times before 4,000 seconds and use the normal intensity for colors after 4,000 seconds. The dim colors before the determined change indicate reduced confidence, and the normal color intensity after the determined change indicates a default level of confidence.

For example, at time 422 and at time 424, the line associated with ULA 404 moves upward and the area indicating intact cerebral autoregulation 406 expands in size. When processing circuitry 110 determines a change in cerebral autoregulation, processing circuitry 110 may be configured to determine the amplitude of change between a previous estimate and an updated estimate of the limit of cerebral autoregulation. At time 422, processing circuitry 110 may determine that the upper limit of cerebral autoregulation has increased by two mmHg. Processing circuitry 110 may be configured to present an indication of the amplitude of change in the limit of cerebral autoregulation in response to determining the amplitude of change between the previous estimate and the updated estimate. Processing circuitry 110 may present, via display 132, text such as "upper limit +2 mmHg".

Graph 400 depicts LLA 402 and ULA 404 at approximately 68 and 75 mmHg, respectively. In response to determining that blood pressure line 410 has a value between 68 and 75 mmHg, processing circuitry 110 may present an indication of an intact cerebral autoregulation status, such as blood pressure line 410 within an area of green color between LLA 402 and ULA 404. Processing circuitry 110 may also present an indication of the intact cerebral autoregulation status such as text (e.g., "autoregulation: intact").

Time period 420 (e.g., the first eight hundred seconds) does not include an indication of LLA 402 or ULA 404 because processing circuitry 110 may not yet have obtained sufficient data to determine LLA 402 or ULA 404. When blood pressure line 410 drops below 60 mmHg, processing circuitry 110 determines and presents LLA 402 on graph 400. When blood pressure line 410 increases above 80 mmHg, processing circuitry 110 determines and presents ULA 404 on graph 400.

Figure 5:
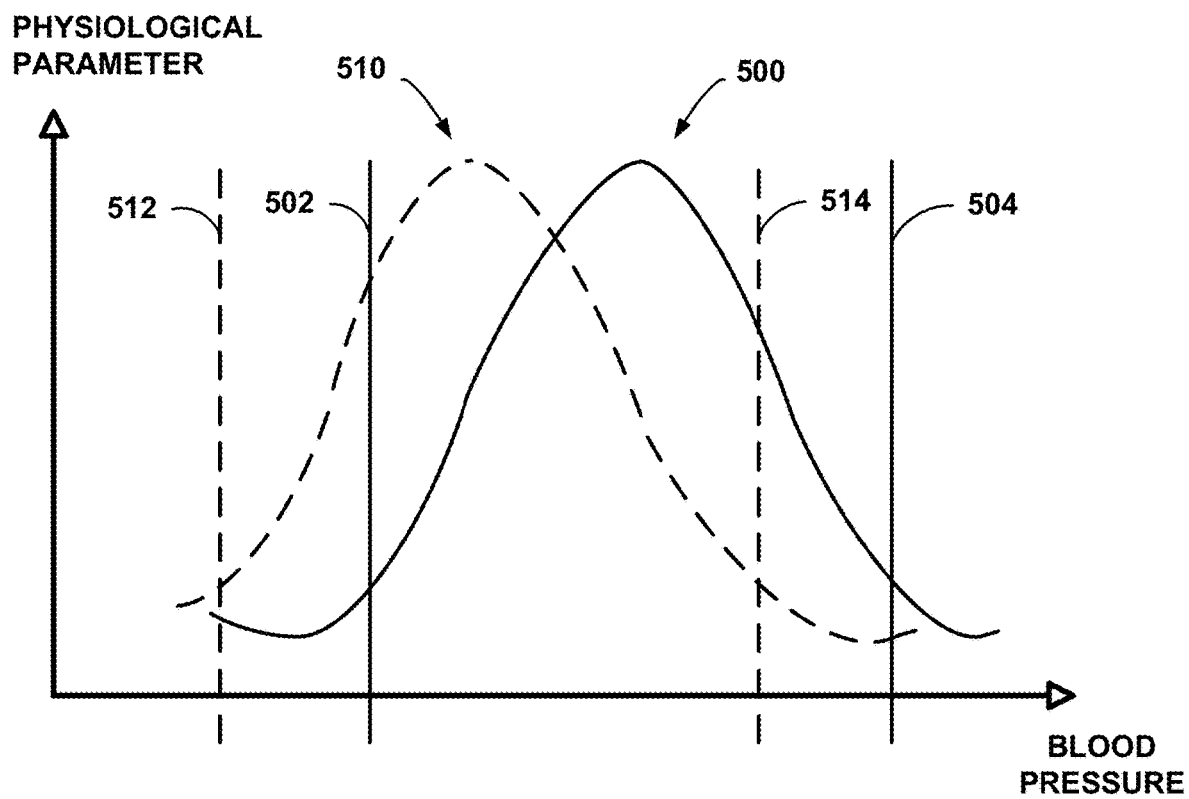
FIGS. 5 and 6 are graphs illustrating example changes in a physiological parameter.
Figure 6:
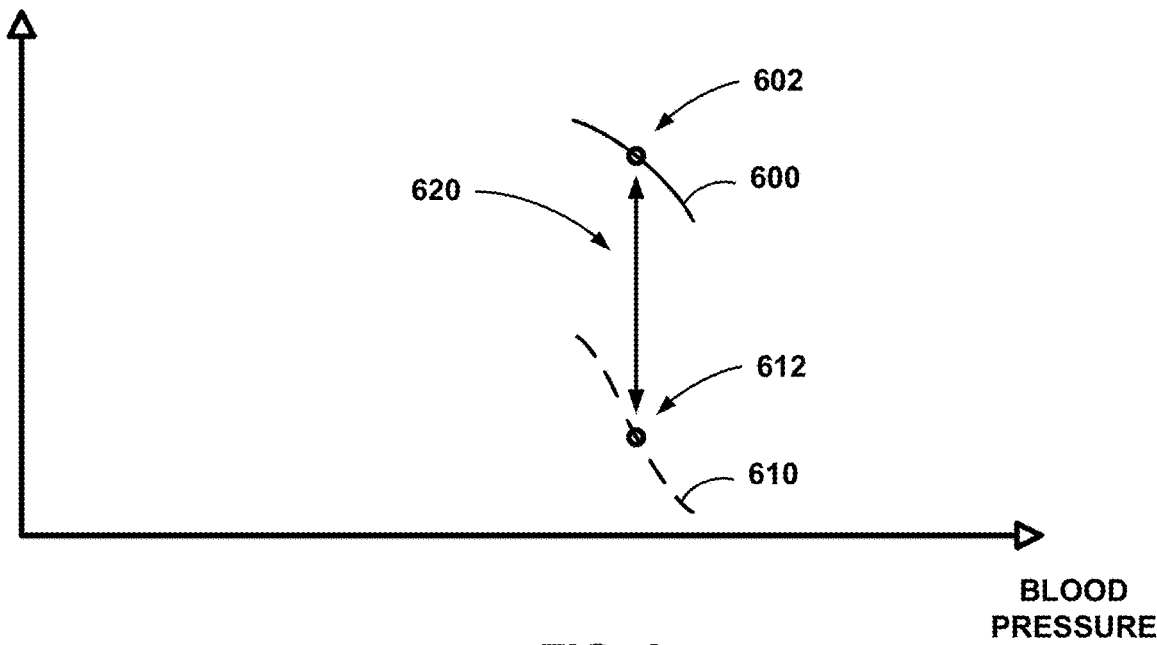

FIGS. 5 and 6 are graphs illustrating example changes in a physiological parameter with respect to blood pressure. Processing circuitry 110 may use relationships 500, 510, 600, and 610 to determine expected values of the physiological parameter and limits of cerebral autoregulation 502, 504, 512, and 514 (e.g., lower limits of autoregulation and upper limits of autoregulation). Processing circuitry 110 is configured to store relationships 500, 510, 600, and 610 to memory 120 as a functional relationship between the blood pressure of a patient and the physiological parameter of the patient. In some examples, processing circuitry 110 may present, via display 132, the curves of relationship 500, 510, 600, and 610 to a user. Processing circuitry 110 may also present indications of the most recently determined blood pressure value and estimates of the limits of cerebral autoregulation (e.g., the LLA and ULA).

Each of relationships 500, 510, 600, and 610 may also include a function such as an exponential function, a polynomial function, a trendline, and/or any other functional relationship. Processing circuitry 110 may determine an expected value of the physiological parameter by inputting a blood pressure value into a functional relationship of relationships 500, 510, 600, and 610, wherein the output of the functional relationship is the expected value of the physiological parameter.

The example of FIG. 5 depicts relationships 500 and 510 as curves on a plot of blood pressure and a physiological parameter of a patient. The curves of relationships 500 and 510 may represent confidence that the cerebral autoregulation is intact. Higher values in the graphs of FIGS. 5 and 6 indicate higher confidence that the cerebral autoregulation is intact, and lower levels indicate higher confidence that the cerebral autoregulation is impaired. Thus, the curves of relationships 500 and 510 are similar to an inverted graph of COx values.

The graph of FIG. 5 may represent a vertical cut through the data in FIG. 4 at a particular reporting time. The curves of relationships 500 and 510 are approximately bell-shaped, but the curves may have any other shape that represents the relationship between the physiological parameter and blood pressure. For example, if the physiological parameter is COx, the curves may instead have an inverted bell shape. Based on relationship 500 shown as a solid line, processing circuitry 110 determines LLA 502 and ULA 504. In response to determining relationship 510 (shown as a dashed line) indicating a change in the cerebral autoregulation of the patient from relationship 500, processing circuitry 110 may determine new limits of cerebral autoregulation, shown as LLA 512 and ULA 514 which have both shifted downward, or to lower blood pressure values, from LLA 502 and ULA 504, respectively.

In response to determining a change in the cerebral autoregulation from relationship 500 to relationship 510, processing circuitry 110 may be configured to generate an alert representative of the change in the cerebral autoregulation. The alert may be presented as including text, a color, audio, and/or any other suitable notification to a user. Processing circuitry 110 may be configured to present the alert via display 132 by presenting the text or color on graphical user interface 300 or graph 400. For example, processing circuitry 110 may present autoregulation status indicator 350 with blinking text or a blinking color in response to determining the change in the cerebral autoregulation of the patient.

Another regional oximetry device may not be able to determine a change in limits of cerebral autoregulation 502 and 504 unless the blood pressure of a patient crosses one of limits of cerebral autoregulation 502 and 504. In contrast, processing circuitry 110 may be able to determine a change from relationship 500 to relationship 510 without the blood pressure of the patient crossing either of limits of cerebral autoregulation 502 or 504. Processing circuitry 110 may be configured to monitor the cross-sectional morphology of relationships 500 and 510 in order to determine a change in the cerebral autoregulation system of the patient. In other words, plots of blood pressure to the physiological parameter that do not fall on the expected relationship 500 indicate that the subject's autoregulation, and the respective LLA and ULA, has likely shifted.

In some examples, processing circuitry 110 may be configured to determine a target blood pressure value based on relationship 500 or 510. In some examples, the target blood pressure value is positioned at a predetermined characteristic point on the relationship curve, such as a peak value of the physiological parameter (e.g., the peak of relationship 500 or 510). In some examples, the predetermined characteristic point on the relationship curve may be a trough value of the physiological parameter. Processing circuitry 110 may be configured to determine a change from relationship 500 to a new or updated relationship, such as relationship 510 shown in FIG. 5, in response to determining a change in the target blood pressure. Processing circuitry 110 may also be configured to determine an updated estimate of a limit of cerebral autoregulation.

FIG. 6 depicts a change in the cerebral autoregulation that processing circuitry 110 may detect even over a short period of time and/or when the blood pressure is entirely within the intact zone (e.g., not crossing a limit of cerebral autoregulation). FIG. 6 depicts only one point (values 602 and 612) on each of relationships 600 and 610, which processing circuitry 110 may be able to use to extrapolate an entire relationship between blood pressure and the physiological parameter. For example, processing circuitry 110 may be able to determine a change in relationship 600 based only on localized information (e.g., actual values in a narrow range) such as value 612, along with the corresponding expected values such as value 602.

Processing circuitry 110 may thus be configured to determine a change from relationship 600 to relationship 610 based on determining a difference between expected value 602 and actual value 612. Processing circuitry 110 may be configured to determine that relationship 600 has shifted to the left (e.g., lower blood pressure values) or shifted to the right (e.g., higher blood pressure values) in response to determining that actual value 612 is not equal to expected value 602. Processing circuitry 110 can determine a change in a limit of cerebral autoregulation based on whether relationship 610 has a higher expected value or a lower expected value than relationship 600 at a particular blood pressure value. In some examples, processing circuitry 110 can also determine that a relationship has shifted to lower values or higher values of the physiological parameter or has compressed or expanded along the blood-pressure axis and/or along the physiological-parameter axis (see Equation (3) above).

In some examples, processing circuitry 110 may determine two or more expected values along the curve of relationship 600 and two or more actual values. Processing circuitry 110 may then determine a collective difference between the two or more actual values and the two or more expected values. Processing circuitry 110 can determine a change (e.g., a curve such as relationship 610) based on the collective difference and the two or more actual values. Processing circuitry 110 may determine relationship 610 to fit the two or more actual values of the physiological parameter. Processing circuitry 110 may assign a confidence measure to relationship 610 based on the number of actual values used to determine relationship 610. Thus, processing circuitry 110 can assign a higher confidence measure to relationship 610 as more values are traced out on the new cerebral autoregulation curve, e.g., over a short period of time. In this manner, processing circuitry 110 may adjust the cerebral autoregulation curve, represented by relationship 500, and associated LLA and/or ULA values based on patient data even if the patient remains within an intact autoregulation status.

Figure 7:
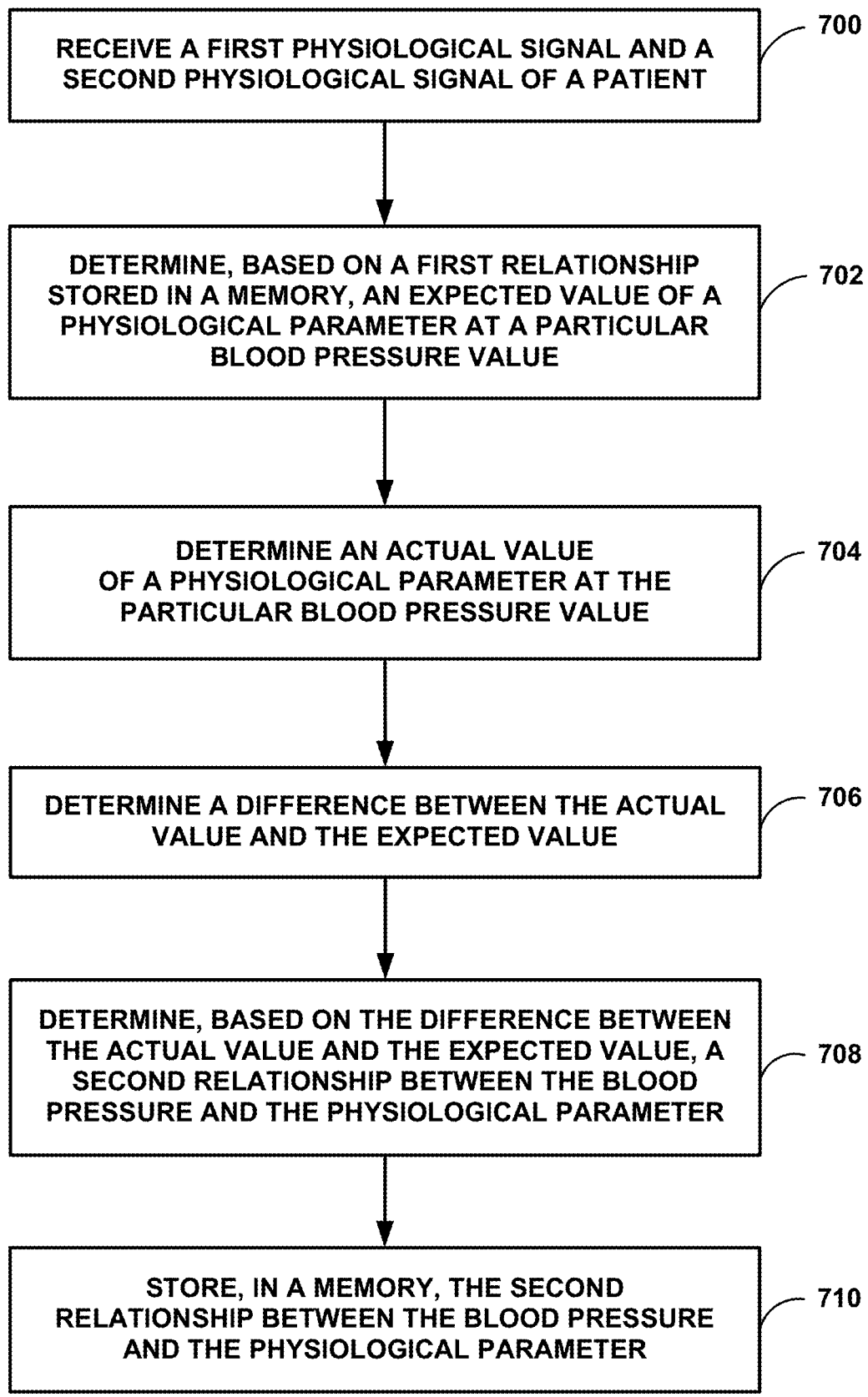
FIG. 7 is a flow diagram illustrating example techniques for determining a change in a limit of autoregulation, in accordance with some examples of this disclosure.

FIG. 7 is a flow diagram illustrating example techniques for determining a change in a limit of autoregulation, in accordance with some examples of this disclosure. Although FIG. 7 is described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIG. 7.

In the example of FIG. 7, processing circuitry 110 receives a first physiological signal and a second physiological signal of a patient from sensing circuitry 140, 141, and/or 142 (700). Sensing circuitry 140, 141, and/or 142 may pre-process physiological signals of the patient received from sensing devices 150, 151, and/or 152 before delivering the processed signals to processing circuitry 110. In some examples, processing circuitry 110 receives the physiological signals directly from sensing devices 150, 151, and/or 152.

In the example of FIG. 7, processing circuitry 110 determines, based on a first relationship stored in memory 120, an expected value of a physiological parameter at a particular blood pressure value (702). Processing circuitry 110 can determine the blood pressure of the patient based on the first physiological signal received from sensing circuitry 140, 141, or 142. Processing circuitry 110 can input the particular blood pressure value to the first relationship in order to generate the expected value of the physiological parameter.

In the example of FIG. 7, processing circuitry 110 determines, based on the first physiological signal, an actual value of the physiological parameter at the particular blood pressure value (704). For example, if the physiological parameter is a COx measure, processing circuitry 110 first determines the oxygen saturation value at the particular blood pressure value based on the second physiological signal and then determine the associated COx value.

Processing circuitry 110 then determines the difference between the actual value and the expected value (706). The difference (e.g., difference 620 shown in FIG. 6) may indicate a change in the patient state from the first relationship to a new relationship between the physiological parameter and the blood pressure of a patient. In some examples, processing circuitry 110 is configured to determine that the difference is greater than a threshold value. In response to determining that the difference is greater than the threshold value instead of less than the threshold value, processing circuitry 110 can determine that the relationship between the physiological parameter and blood pressure has changed. A small difference may be caused by noise or natural variability. Thus, processing circuitry 110 may be configured to determine a change in relationship only for a sufficiently large difference.

Where processing circuitry 110 is described herein as determining that a value is less than or equal to another value, this description may also include processing circuitry 110 determining that a value is only less than the other value. Similarly, where processing circuitry 110 is described herein as determining that a value is less than another value, this description may also include processing circuitry 110 determining that a value is less than or equal to the other value. The same properties may also apply to the terms "greater than" and "greater than or equal to."

In the example of FIG. 7, processing circuitry 110 determines, based on the difference between the actual value and the expected value, a second relationship between the blood pressure and the physiological parameter (708). Processing circuitry 110 can determine the second relationship as a shifted, compressed, and/or expanded version of the first relationship. Processing circuitry 110 then stores, in memory 120, the second relationship between the blood pressure and the physiological parameter (710). Processing circuitry 110 can store the second relationship as polynomial function, an exponential function, and/or any other functional relationship or curve relating blood pressure values and values of the physiological parameter.

Processing circuitry 110 may be configured to determine a first estimate of a limit of cerebral autoregulation based on the first relationship. For example, processing circuitry 110 may estimate the lower limit of cerebral autoregulation at the lowest blood pressure value at which the expected value of the physiological parameter, based on the first relationship, is greater than, or less than, a threshold value. In response to determining the second relationship, processing circuitry 110 may be configured to determine an updated estimate of the limit of cerebral autoregulation (e.g., LLA and/or ULA) based on the second relationship, where the updated estimate of the limit of cerebral autoregulation may be different from a previous estimate of the limit of cerebral autoregulation associated with the first relationship.

Processing circuitry 110 can use the change between the first estimate and the updated estimate of the limit of cerebral autoregulation to determine a change in a second limit of cerebral autoregulation. For example, if processing circuitry 110 determines that the lower limit of cerebral autoregulation has decreased by five mmHg, processing circuitry 110 may be configured to determine that the upper limit of cerebral autoregulation has also decreased by five mmHg. Alternatively, processing circuitry 110 can determine that the distance between the limits of cerebral autoregulation has changed such that both limits of cerebral autoregulation do not shift by an equal amount when processing circuitry 110 determines an updated relationship (e.g., the second relationship may be a compressed or expanded version of the first relationship).

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:
1. A device comprising:
   a memory configured to store a first relationship between a blood pressure of a patient and a physiological parameter of the patient, the physiological parameter being different than the blood pressure, the first relationship being indicative of cerebral autoregulation of the patient; and processing circuitry configured to:
receive a first physiological signal indicative of the blood pressure of the patient; and
receive a second physiological signal indicative of the physiological parameter of the patient;
determine, based on the first relationship, an expected value of the physiological parameter at a particular blood pressure value of the first physiological signal;
determine an actual value of the physiological parameter from the second physiological signal at the particular blood pressure value of the first physiological signal;
determine a difference between the actual value of the physiological parameter and the expected value of the physiological parameter;
determine, based on the difference between the actual value and the expected value, a second relationship between the blood pressure of the patient and the physiological parameter of the patient, the second relationship being indicative of a change in the cerebral autoregulation of the patient from the first relationship; and
store, in the memory, the second relationship between the blood pressure of the patient and the physiological parameter of the patient.

2. The device of claim 1, wherein the processing circuitry is further configured to:
determine two or more expected values of the physiological parameter at two or more respective blood pressure values of the first physiological signal;
determine two or more actual values of the physiological parameter from the second physiological signal at the two or more respective blood pressure values of the first physiological signal; and
determine a collective difference between the two or more actual values of the physiological parameter and the two or more expected values of the physiological value,
wherein the processing circuitry is configured to determine the second relationship between the blood pressure of the patient and the physiological parameter of the patient based on the collective difference.

3. The device of claim 1, wherein the processing circuitry is further configured to:
determine whether the second relationship has a higher expected value of the physiological parameter or a lower expected value of the physiological parameter than the first relationship at the particular blood pressure value; and
determine a change in a limit of cerebral autoregulation based on whether the second relationship has the higher expected value or the lower expected value of the physiological parameter at the particular blood pressure value.

4. The device of claim 1,
wherein the processing circuitry is configured to determine the second relationship by at least determining an updated estimate of a limit of cerebral autoregulation with respect to the blood pressure of the patient,
wherein the updated estimate of the limit of cerebral autoregulation is associated with the second relationship, and
wherein the updated estimate of the limit of cerebral autoregulation is different from a previous estimate of the limit of cerebral autoregulation associated with the first relationship.

5. The device of claim 4,
wherein the updated estimate of the limit of cerebral autoregulation is an updated estimate of a first limit of cerebral autoregulation,
wherein the previous estimate of the limit of cerebral autoregulation is a previous estimate of the first limit of cerebral autoregulation, and
wherein the processing circuitry is further configured to determine, based on a difference between the updated estimate of the first limit of cerebral autoregulation and the previous estimate of the first limit of cerebral autoregulation, a change in a second limit of cerebral autoregulation.

6. The device of claim 1, further comprising a display, wherein the processing circuitry is further configured to:
determine the change in the cerebral autoregulation by at least determining an amplitude of change between a previous estimate of a limit of cerebral autoregulation and an updated estimate of the limit of cerebral autoregulation; and
present an indication of the amplitude of change in the limit of cerebral autoregulation.

7. The device of claim 1, further comprising a display, wherein the processing circuitry is further configured to present, via the display, an indication of the second relationship.

8. The device of claim 7, wherein the processing circuitry is further configured to:
determine a cerebral autoregulation status of the patient based on the second relationship and the blood pressure of the patient, and
present, via the display, an indication of the cerebral autoregulation status.

9. The device of claim 8, wherein the processing circuitry is further configured to:
determine a change in a limit of cerebral autoregulation in response to determining the second relationship;
present, via the display, an indication of the cerebral autoregulation status as a color; and
change the intensity of the color in response to determining the change in the limit of cerebral autoregulation.

10. The device of claim 9, wherein the processing circuitry is configured to change the intensity of the color by at least changing the intensity of the color based on a magnitude of the change in the limit of cerebral autoregulation.

11. The device of claim 1, wherein the processing circuitry is further configured to:
determine a target blood pressure based on the first physiological signal; and
determine a change in the target blood pressure based on a change in the first physiological signal,
wherein the processing circuitry is configured to, responsive to determining the change in the target blood pressure, determine, based on the change in the target blood pressure, the second relationship and at least one of an updated estimate of a lower limit of cerebral autoregulation or updated estimate of an upper limit of cerebral autoregulation.

12. The device of claim 1, further comprising a display, wherein the processing circuitry is further configured to:
responsive to determining the change in the cerebral autoregulation from the first relationship to the second relationship, generate an alert representative of the change in the cerebral autoregulation; and
present, via the display, the alert.

13. The device of claim 1, wherein the physiological parameter comprises a confidence in a metric representative of the cerebral autoregulation of the patient.

14. The device of claim 1, wherein the processing circuitry is further configured to:
determine that the difference between the actual value and the expected value is greater than a threshold value; and
responsive to determining that the difference between the actual value and the expected value is greater than the threshold value instead of less than the threshold value, determine the second relationship between the blood pressure of the patient and the physiological parameter of the patient.

15. A method comprising:
storing, in a memory, a first relationship between a blood pressure of a patient and a physiological parameter of the patient, the physiological parameter being different than the blood pressure, the first relationship being indicative of cerebral autoregulation of the patient;
receiving, by processing circuitry, a first physiological signal indicative of the blood pressure of the patient;
receiving, by the processing circuitry, a second physiological signal indicative of the physiological parameter of the patient;
determining, by the processing circuitry and based on the first relationship, an expected value of the physiological parameter at a particular blood pressure value of the first physiological signal;
determining, by the processing circuitry, an actual value of the physiological parameter from the second physiological signal at the particular blood pressure value of the first physiological signal;
determining, by the processing circuitry, a difference between the actual value of the physiological parameter and the expected value of the physiological parameter;
determining, by the processing circuitry and based on the difference between the actual value and the expected value, a second relationship between the blood pressure of the patient and physiological parameter of the patient, the second relationship being indicative of a change in the cerebral autoregulation of the patient from the first relationship; and
storing, in the memory, the second relationship between the blood pressure of the patient and the physiological parameter of the patient.

16. The method of claim 15, further comprising:
determining two or more expected values of the physiological parameter at two or more respective blood pressure values of the first physiological signal;
determining two or more actual values of the physiological parameter from the second physiological signal at the respective two or more blood pressure values of the first physiological signal; and
determining a collective difference between the two or more actual values of the physiological parameter and the two or more expected values of the physiological value,
wherein determining the second relationship between the blood pressure of the patient and the physiological parameter of the patient is based on the collective difference.

17. The method of claim 15, further comprising:
determining whether the second relationship has a higher expected value of the physiological parameter or a lower expected value of the physiological parameter than the first relationship at the particular blood pressure value; and
determining a change in a limit of cerebral autoregulation based on whether the second relationship has the higher expected value or the lower expected value of the physiological parameter at the particular blood pressure value.

18. The method of claim 15, further comprising:
determining a change in a limit of cerebral autoregulation in response to determining the second relationship;
determining a cerebral autoregulation status of the patient based on the second relationship and the blood pressure of the patient;
presenting, via the display, an indication of the cerebral autoregulation status as a color; and
changing the intensity of the color in response to determining the change in the limit of cerebral autoregulation.

19. The method of claim 15, further comprising:
determining a target blood pressure based on the first physiological signal; and
determining a change in the target blood pressure based on a change in the first physiological signal,
wherein determining the second relationship is responsive to determining the change in the target blood pressure.

20. A device comprising:
a display;
a memory configured to store a first relationship between a blood pressure of a patient and a physiological parameter of the patient, the physiological parameter being different than the blood pressure, the first relationship being indicative of cerebral autoregulation of the patient;
sensing circuitry configured to:
receive a first physiological signal indicative of the blood pressure of the patient; and
receive a second physiological signal indicative of the physiological parameter of the patient; and
processing circuitry configured to:
determine, based on the first relationship, an expected value of the physiological parameter at a particular blood pressure value of the first physiological signal;
determine an actual value of the physiological parameter from the second physiological signal at the particular blood pressure value of the first physiological signal;
determine a difference between the actual value of the physiological parameter and the expected value of the physiological parameter;
determine, based on the difference between the actual value and the expected value, a second relationship between the blood pressure of the patient and the physiological parameter of the patient, the second relationship being indicative of change in the cerebral autoregulation of the patient from the first relationship;
determine a lower limit of cerebral autoregulation and an upper limit of cerebral autoregulation based on the second relationship, wherein blood pressure values between the lower limit of cerebral autoregulation and the upper limit of cerebral autoregulation indicate a blood pressure range representative of intact cerebral autoregulation for the patient;
present, via the display, an indication of the cerebral autoregulation status based on the lower limit of cerebral autoregulation and the upper limit of cerebral autoregulation; and
store, in the memory, the second relationship between the blood pressure of the patient and the physiological parameter of the patient.

* * * * *